United States Patent
Gann et al.

(10) Patent No.: US 8,062,639 B2
(45) Date of Patent: Nov. 22, 2011

(54) ANTIBODIES TO BUFALIN PREVENT INHIBITION OF NA/K ATPASE AND PROLONG SURVIVAL IN SHOCK

(76) Inventors: Donald Stuart Gann, Lutherville, MD (US); Daniel Norman Darlington, Schertz, TX (US)

(*) Notice: Subject to any disclaimer, the term of this patent is extended or adjusted under 35 U.S.C. 154(b) by 348 days.

(21) Appl. No.: 12/319,967

(22) Filed: Jan. 14, 2009

(65) Prior Publication Data

US 2009/0181031 A1    Jul. 16, 2009

Related U.S. Application Data

(60) Provisional application No. 61/021,349, filed on Jan. 16, 2008.

(51) Int. Cl.
*A61K 39/395*    (2006.01)

(52) U.S. Cl. ............... 424/145.1; 424/141.1; 424/130.1

(58) Field of Classification Search .................. None
See application file for complete search history.

(56) References Cited

U.S. PATENT DOCUMENTS

2006/0134106 A1*    6/2006   Adair ..................... 424/133.1

* cited by examiner

*Primary Examiner* — Sharon Wen

(57) ABSTRACT

The present invention relates to compositions and methods of use thereof for treatment of clinical conditions manifested from and/or exacerbated by a decrease or an inhibition of Na/K ATPase activity. The invention relates to composition comprises monoclonal or polyclonal antibodies to bufalin and/or bufalin sulfate, or vaccination against bufalin and/or bufalin sulfate, which prevents or attenuates inhibition of Na/K ATPase activity thereby attenuating the adverse physiological effects of bufalin and/or bufalin sulfate inhibition. The invention also relates to methods of treating hemorrhagic, septic shock, cardiogenic shock, shock resulting from physical trauma, diabetes, mental depression, bipolar disorder and schizophrenia comprising administering a therapeutically effective amount of an bufalin monoclonal or polyclonal antibody.

25 Claims, 4 Drawing Sheets

Figure 1:
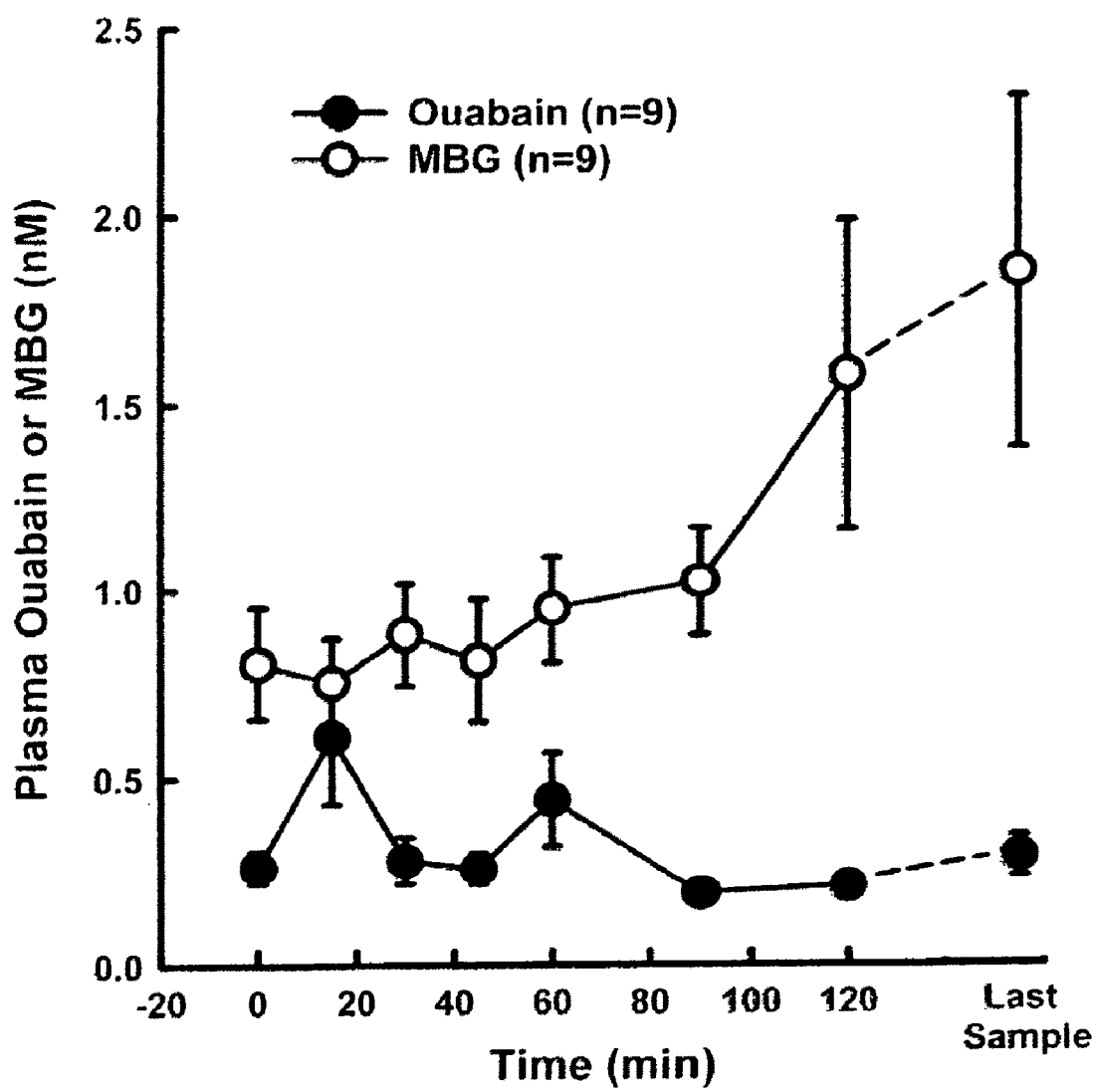

ANTIBODIES TO BUFALIN PREVENT INHIBITION OF NA/K ATPASE AND PROLONG SURVIVAL IN SHOCK

This application claims priority from Provisional Application, U.S. Ser. No. 61/021,349, filed, Jan. 16, 2008.

FIELD OF THE INVENTION

The invention is related to the fields of medicine, cell biology, and physiology. The invention further relates to methods and compositions for treating clinical conditions that manifest as an inhibition or a decrease in Na/K ATPase activity.

BACKGROUND OF THE INVENTION

Hemorrhagic Shock

Severe hemorrhagic shock is associated with an elevation in plasma potassium, a decrease in transmembrane potential and an increase in cell swelling (1-13), all of which have been attributed to a decrease in the activity of sodium-potassium adenosine triphosphatase (Na/K ATPase) by an inhibitor in the circulation during shock (10-14). Septic shock or shock caused by cardiac insufficiency is also associated with a decrease in the activity of Na/K ATPase. (2-4, 10, 11). Na/K ATPase is defined operationally as that fraction of Na and K transport that can be inhibited by ouabain. Endogenous inhibitors of Na/K ATPase have been reported by many laboratories (20, 27-30) including ours (11-12, 21). These endogenous inhibitors appear in plasma, urine and tissue in various clinical conditions including hemorrhagic and septic shock, heart failure, myocardial depression, and diabetes (11-13, 27, 28). Shires et al. (9) reported that septic shock in adult baboons induced a decrease in membrane potential in skeletal muscle and in red blood cells (RBCs) along with a rise in intracellular Na, Cl, and $H_2O$, and a decrease in intracellular K. Our laboratory has also reported depolarization and cell swelling in both hemorrhagic and septic shock in rats and dogs (10-13, 21). The movement of $H_2O$, Na, and Cl into cells and out of the extracellular space contributes to the fall in blood volume and blood pressure seen in hemorrhagic shock, and probably explains why resuscitation with volumes larger than those lost during hemorrhage are necessary for cardiovascular stabilization.

Hemorrhagic shock is a life-threatening condition brought on by severe blood loss. For example, hemorrhagic shock may originate from internal or external hemorrhage, gun shot wounds, severe trauma, or any other condition associated with blood loss. Unfortunately, because of the severity and complexity of hemorrhagic shock, a patient is likely to die unless treated during a relatively short treatment window, generally known as the "golden hour." Hemorrhagic shock is an extremely complex process involving multiple pathways. Changes that have been observed include the release of cytokines, superoxide radicals, elements of the clotting cascade, neuroendocrine and classical stress hormones, and subsequent metabolic and electrolyte factors. In light of this, the treatment of a patient in hemorrhagic shock can be extremely complex.

The initial phase of hemorrhagic shock, unless rapidly corrected, is followed by progressive tissue ischemia, end-organ dysfunction and refractory vascular failure. Hemorrhagic shock also is associated with early vasomotor paralysis and cardiovascular collapse. Accordingly, conventional resuscitation methods have been directed toward hemostasis and intravenous infusion of sufficiently large volumes of fluid, usually Ringers lactate or blood, in order to restore cardiac index, improve oxygen delivery, and minimize cellular hypoxia.

Bufalin:

Bufalin is a potent inhibitor of Na/K ATPase and a member of the bufadienolide family originally isolated from the tissues and body fluid of toads of the genus bufo (31, 32). Bufalin and other bufadienolides inhibit Na/K ATPase, and have been measured in plasma from mammals (33-36). Inhibition of Na/K ATPase leads to an accumulation of intracellular Na, which then activates the Na/Ca exchanger whereby an elevation in intracellular Ca ensues.

Plasma bufadienolides are elevated in patients with preeclampsia. Bufadienolides have been shown to cause vasoconstriction of human mesenteric smooth muscle. In pregnant rats, experimental preeclampsia induced with deoxycorticosterone acetate (DOCA) and salt loading causes hypertension similar to preeclampsia, and can be attenuated with antibodies to bufadienolides (37-41). Bufadienolides have been implicated in the development of various forms of hypertension. In humans, salt loading elevates plasma bufadienolides (42). In rat models of hypertension, bufadienolides are elevated in NaCl-loaded Dahl-S hypertensive rats (43). NaCl loading causes hypertension in these rats that eventually progresses to ventricular hypertrophy and failure. Bufadienolides are elevated during the development of hypertension, and elevated during the development of cardiac hypertrophy and failure (44-46). Salt loading in normal rats causes an elevation in the excretion of bufadienolides and inhibition of proximal tubule Na/K ATPase can be reversed by antibodies to bufadienolides (47).

Bufadienolides are elevated in humans in a variety of disease states including renal failure (48). Bufadienolides are also elevated in rats with experimental renal failure (partial nephrectomy) (49). In experimental renal failure in rats. Bufadienolides increase-production of collagen in cardiac fibroblasts and are involved in cardiac failure and hypertrophy (50). Plasma Bufadienolides are elevated in human patients with congestive heart failure (51), chronic renal failure, primary aldosteronism, and essential hypertension (52). The elevation of bufadienolides may be triggered by volume expansion in these disease states as plasma bufadienolides have been shown to be elevated during acute volume expansion in anesthetized rats and dogs (53,54). Bufadienolides are present in human urine after myocardial infarcts (55,56) and are also elevated in rats with experimental diabetes mellitus (57). Bufadienolides have been implicated in alcohol addiction. Bufadienolides, ouabain and digoxin, suppress the free choice of alcohol in Wistar rats, whereas immunization against bufadienolides, ouabain and digoxin is associated with alcohol seeking behavior (58).

The control of bufadienolides secretion is not well understood. ACTH has been shown to stimulate adrenal bufadienolides secretion in rats (59). In salt sensitive Dahl rats, NaCl loading has been shown to stimulate brain ouabain, which than activates angiotensin II to stimulate adrenocortical bufadienolides (60). There is evidence showing that Protein Kinase C (PKC) increases the sensitivity of bufadienolides by phosphorylating alpha-1 Na/K-ATPase. Inhibitors of PKC (Cicletanine) attenuate-Na/K-ATPase inhibition by bufadienolides as well as bufadienolide-induced vasoconstriction of human mesenteric artery rings (61-63).

SUMMARY OF THE INVENTION

The invention relates to methods and compositions affecting Na/K ATPase activity in a cell. The invention further relates to methods and compositions for treating conditions caused by a decrease or inhibition of Na/K ATPase.

In certain embodiments, the invention is drawn to a method of treating a pathological condition or disease in a subject in need thereof which is caused by an alteration in Na/K ATPase activity. In specific embodiments, the invention is drawn administering a composition comprising a therapeutically effect amount of a molecule that decreases or inhibits a biological activity of a bufadienolide. In other specific embodiments, an alteration in Na/K ATPase activity is a decrease or inhibition of said activity. In other specific embodiments, a molecule of the invention includes a polyclonal antibody, a monoclonal antibody, or antigen binding fragment thereof. In further specific embodiments, the molecule is a polyclonal antibody. In other further specific embodiments, the molecule is a monoclonal antibody. In other specific embodiments, a bufadienolide is bufalin and/or bufalin sulfate. In other specific embodinents, the molecule is an antigen that stimulates the immune system to create antibodies against bufadienolides thereby acting as a vaccine.

In other embodiments, the invention is drawn to a method of treating a physiological effect in a subject in need thereof, which is caused by an alteration in Na/K ATPase activity. In specific embodiments, the invention is drawn administering a composition comprising a therapeutically effect amount of a molecule that decreases or inhibits a biological activity of a bufadienolide. In other specific embodiments, an alteration in Na/K ATPase activity is a decrease or inhibition of said activity. In other specific embodiments, a molecule of the invention includes a polyclonal antibody, a monoclonal antibody, or antigen binding fragment thereof. In further specific embodiments, the molecule is a polyclonal antibody. In other further specific embodiments, the molecule is a monoclonal antibody. In other specific embodiments, a bufadienolide is bufalin and/or bufalin sulfate. In other specific embodiments, the molecule is an antigen that stimulates the immune system to create antibodies against bufadienolides thereby acting as a vaccine.

In certain embodiments, the invention is drawn to a method of treating shock in a subject in need thereof, which is caused by an alteration in Na/K ATPase activity. In specific embodiments, the invention is drawn administering a composition comprising a therapeutically effect amount of a molecule that decreases or inhibits a biological activity of a bufadienolide. In other specific embodiments, an alteration in Na/K ATPase activity is a decrease or inhibition of said activity. In other specific embodiments, a molecule of the invention includes a polyclonal antibody, a monoclonal antibody, or antigen binding fragment thereof. In further specific embodiments, the molecule is a polyclonal antibody. In other further specific embodiments, the molecule is a monoclonal antibody. In other specific embodiments, a bufadienolide is bufalin and/or bufalin sulfate. In other specific embodiments, the molecule is an antigen that stimulates the immune system to create antibodies against bufadienolides thereby acting as a vaccine.

In other embodiments, the invention is drawn to a method of resuscitating a subject in need thereof. In specific embodiments, the invention is drawn administering a resuscitation fluid comprising a molecule that decreases or inhibits a biological activity of a bufadienolide. In other specific embodiments, a molecule of the invention includes a polyclonal antibody, a monoclonal antibody, or antigen binding fragment thereof. In further specific embodiments, the molecule is a polyclonal antibody. In other further specific embodiments, the molecule is a monoclonal antibody. In other specific embodiments, a bufadienolide is bufalin and/or bufalin sulfate. In other specific embodiments, the molecule is an antigen that stimulates the immune system to create antibodies against bufadienolides thereby acting as a vaccine.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTIONS OF THE DRAWINGS

FIG. 1. The butadienolide, marinobufagenin, is significantly elevated in rat plasma after hemorrhage. Ouabain is not. Marinobufagenin was measured as in index of bufadienolide activity in plasma as this assay is currently the only assay available to measrure bufadienolides) There were 9 rats/group.

Figure 2:
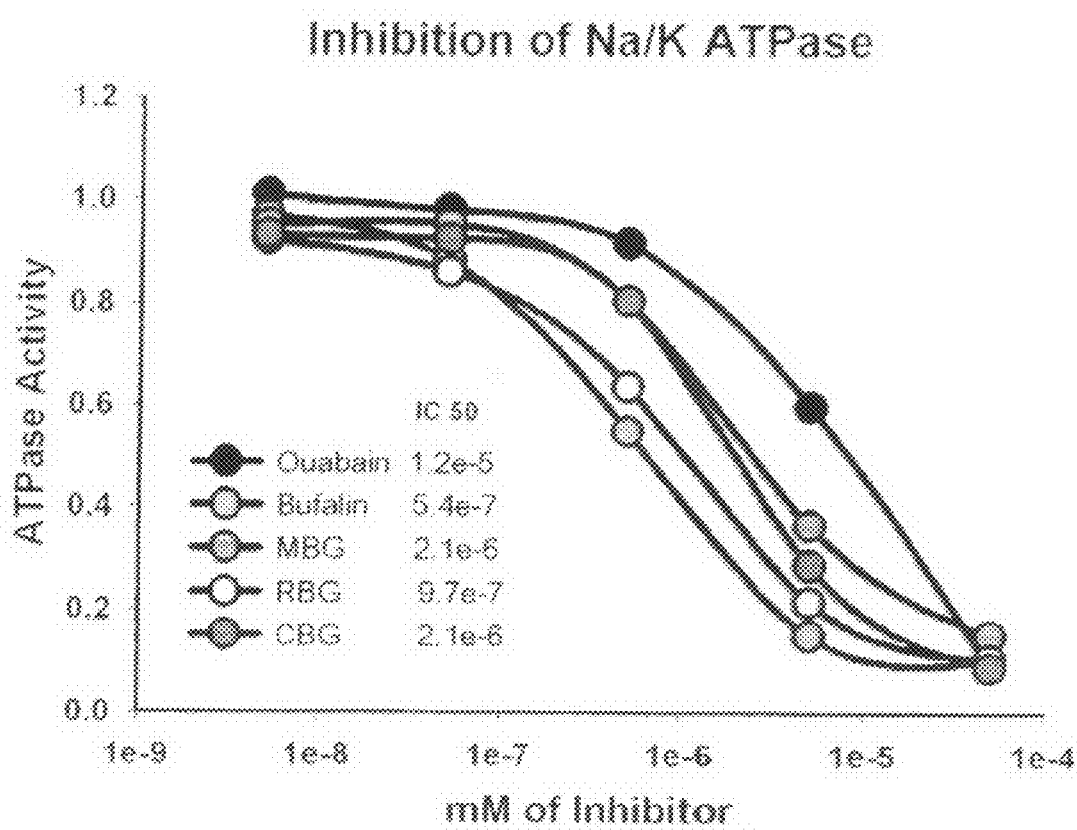

FIG. 2. Bufalin, marinobufogenin (MBG), resibufogenin (RBG), cinobufagin (CBG) (and ouabain) inhibits Na/K ATPase in a dose-response manner. pNPP (paranitrophenyl phosphate) is converted to pNP by Na/K ATPase and the inhibition of this conversion is a function of increasing a therapeutically effective dose of bufadienolides and Ouabain.

Figure 3:
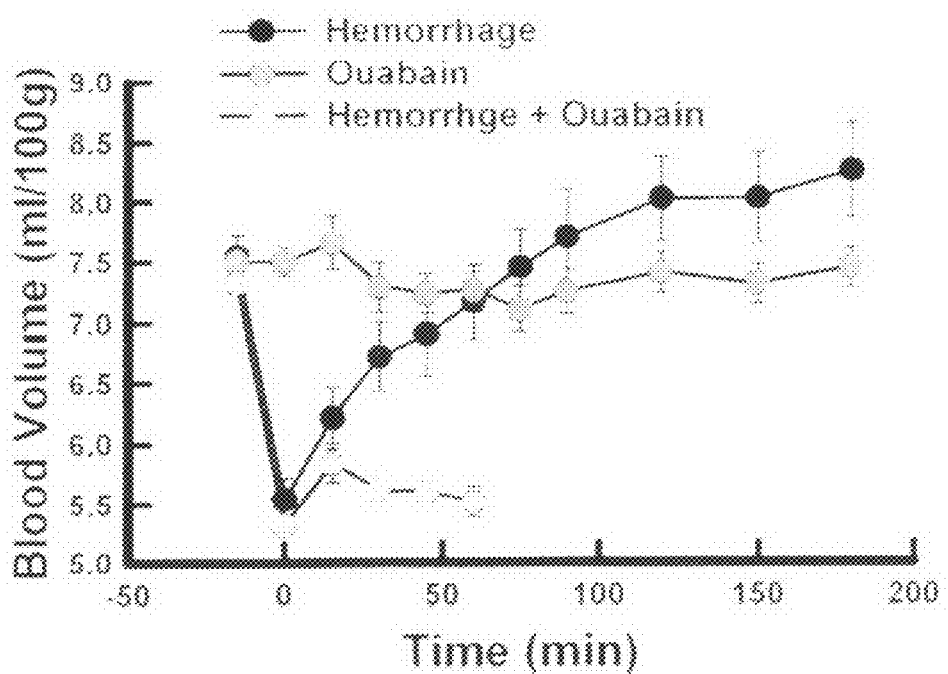
Figure 3:
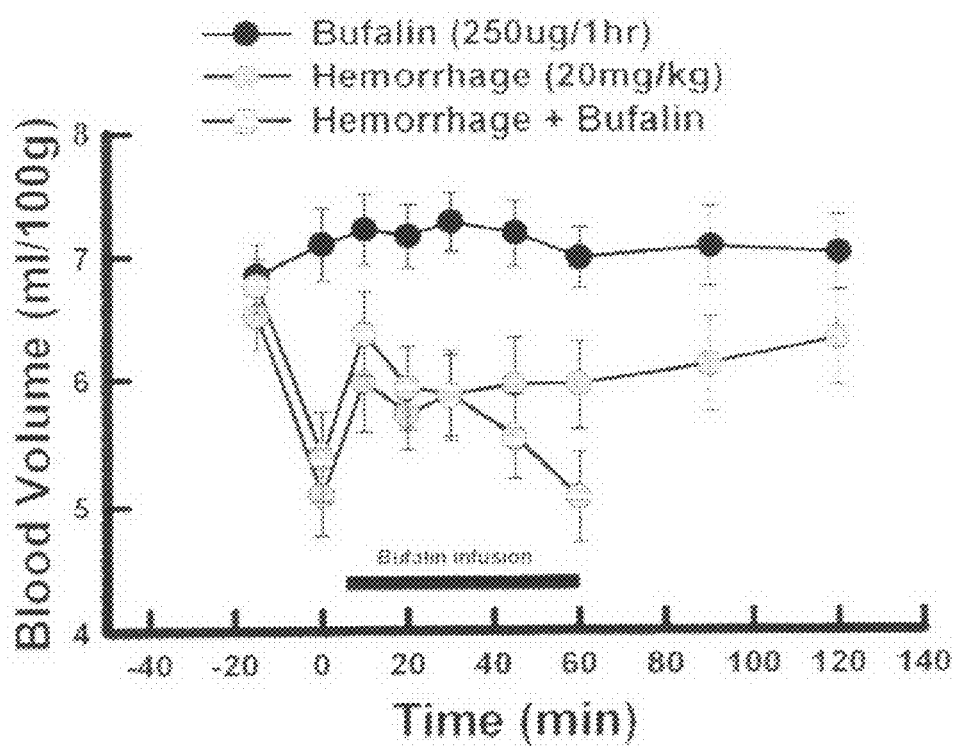

FIG. 3. A) Change in plasma volume in conscious rats with either 1) 20 ml/kg hemorrhage, 2) infusion of 2 mg/ml (5 ml/hr) ouabain or 3) both. B) Change in plasma volume in conscious rats with either 1) 20 ml/kg hemorrhage, 2) infusion of 2 mg/ml (5 ml/hr) bufalin or 3) both. In both graphs, conscious rats restore plasma volume after hemorrhage. However, ouabain (with hemorrhage) or bufalin (with hemorrhage) prevents restoration and leads to death. Ouabain alone or bufalin alone has no effect on plasma volume. There are 8 rats/group.

Figure 4:
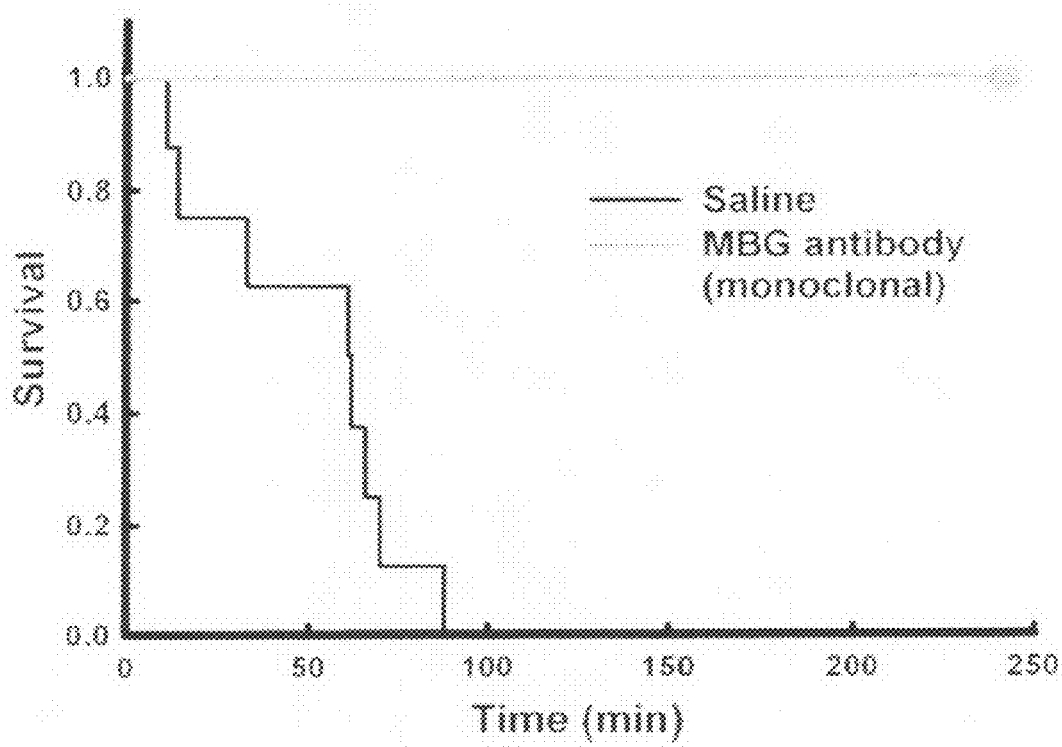
Figure 4:
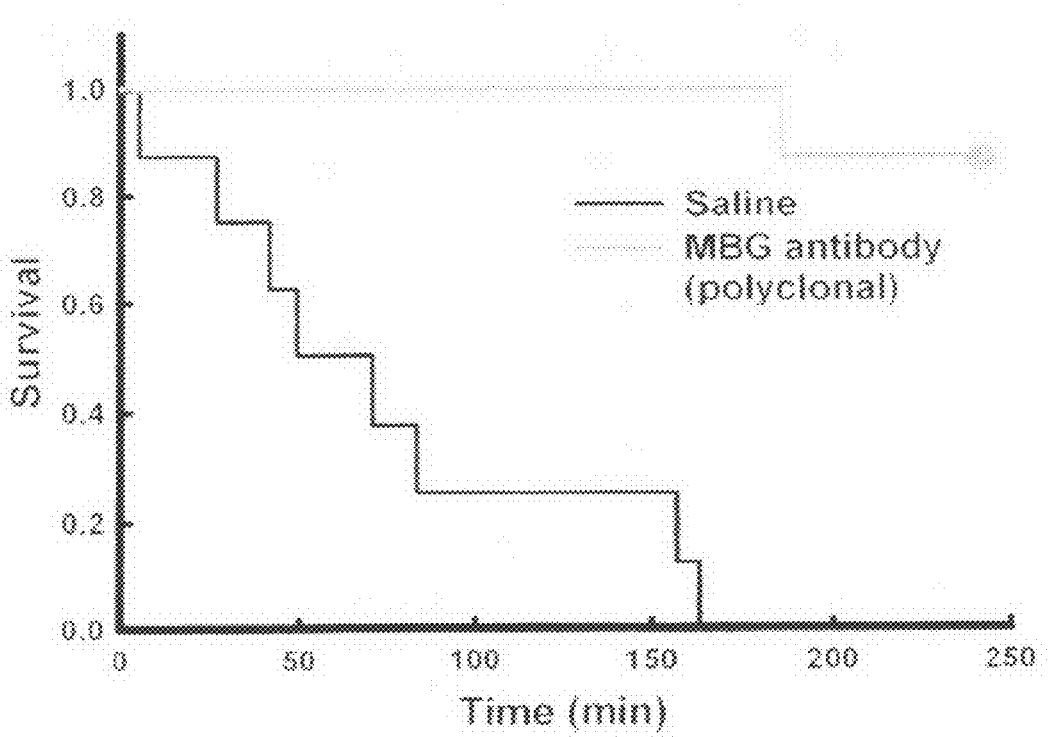

FIG. 4. Mono- and polyclonal antibodies to the bufafienolide, MBG prolong survival to hemorrhagic shock. The polyclonal antibodies were placed on an affinity column and were shown to capture 10× more Bufalin than MBG. Pentobarbital anesthetized rats had mean arterial blood pressure lowered to 35 mmHg by hemorrhage and maintained for 2.5 hr. Resuscitation was with a volume similar to that lost during hemorrhage and contained either monoclonal or polyclonal antibodies (IC75) in saline. Monoclonal antibodies were developed in mice against MBG-BSA. Polyclonal antibodies were developed in rabbits against MBG-BSA and MBG-OvaAlbumin. There were 8 rats/group.

DETAILED DESCRIPTION OF THE INVENTION

I. Definitions

Unless otherwise noted, technical terms are used according to conventional usage. Definitions of common scientific technical terms may be found, for example, in Mcgraw-hill Dictionary of Scientific & Technical Terms published by Mcgraw-hill Healthcare Management Group; Benjamin Lewin, Genes VIII, published by Oxford University Press; Kendrew et al. (eds.), The Encyclopedia of Molecular Biology, published by Blackwell Publishers; and Robert A. Meyers (ed.), Molecular Biology and Biotechnology: a Comprehensive Desk Reference, published by Wiley, John & Sons, Inc; and other similar technical references.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

A "therapeutically effective amount" or a "therapeutic effective amount" is an amount of a molecular entity of the invention that alleviates, totally or partially, the physiological effects of shock. A therapeutically effective amount can also be an amount that is given prophylactically thereby inhibiting any physiological effects of shock. The amount that is therapeutically effective will depend upon, for example, the patient's size, gender, magnitude of the associated condition or injury, and genetic or non-genetic factors associated individual pharmacokinetic and pharmacodynamic profiles of administered molecular entities. For a given subject in need thereof, a therapeutically effective amount can be determined by those of ordinary skill in the art and by methods known to those of ordinary skill in the art.

As used herein, the term "antibody" or "antibodies" includes non-human, human, and humanized polyclonal antibodies, monoclonal antibodies, and antigen-binding fragments, such as, for example, F(ab')2 and Fab proteolytic fragments. Engineered intact antibodies or fragments, such as chimeric antibodies, Fv fragments, single chain variable fragments or antibodies, and the like, as well as synthetic antigen-binding peptides and polypeptides, are also included. Non-human antibodies may be humanized by grafting non-human CDRs onto human framework and constant regions or by incorporating the entire non-human variable domains (optionally "cloaking" them with a human-like surface by replacement of exposed residues wherein the result is a "veneered" antibody). In some instances, humanized antibodies may retain non-human residues within the human variable region framework domains to enhance proper binding characteristics. Through humanizing antibodies, biological half-life may be increased and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

As used herein, the term vaccine includes the use of a molecule (ex, bufadienolide but not limited to bufadienolide) that cause an immune response in humans or animals that prevents inhibition of Na/K ATPase.

II. The Present Invention

A. Invention

In certain embodiments, the invention is drawn to a method of treating a pathological condition or disease in a subject in need thereof, which is caused by an alteration in Na/K ATPase activity. A pathological condition or disease caused by an alteration in Na/K ATPase activity whereby said activity is inhibited or decreased includes a variety of pathological conditions and diseases including, for example, shock (including, for example, hemorrhagic shock, septic shock, cardiogenic shock, and shock caused by physical trauma), cardiovascular associated pathophysiologies (including, for example, myocardial infarction, congestive heart failure, clinically low cardiac output, hypertension, stroke, and preeclampsia), mental or cognitive pathophysiologies (including, for example, depression, schizophrenia, bi-polar disorder, drug or other type of dependence (i.e., addiction), drug seeking behavior, and cognitive decline), diabetes, insulin resistance, fatigue, or any other pathophysiology characterized by an inhibition or decrease in Na/K ATPase activity.

In other embodiments, the invention is drawn to a method of treating a physiological effect in a subject in need thereof, which is caused by an alteration in Na/K ATPase activity. Physiological effects caused by an alteration in Na/K ATPase activity whereby said activity is decreased or inhibited causes a decline in vital processes of a cell and the body including, for example, smooth muscle tone, cardiac output and other muscular activity, maintenance of cellular membrane potential, maintenance of homeostatic intracellular and extracellular aqueous volume (including, for example, renal dependent and renal independent mechanisms), and maintenance of ionic balances (including, for example, intracellular calcium).

In certain embodiments, the invention is drawn to a method of treating shock in a subject in need thereof, which is caused by an alteration in Na/K ATPase activity. It is known by one of ordinary skill in the art that shock is defined as a state of profound depression of the vital processes of the body that is characterized by, for example, pallor, rapid but weak pulse, rapid and shallow respiration, reduced total blood volume, and decreased blood pressure, which is usually caused by severe crushing injuries, hemorrhage, burns, major surgery, or sepsis. The invention is drawn to methods and compositions for treating shock including hemorrhagic shock, septic shock, cardiogenic shock, and/or shock that may result from physical trauma (including, for example, blunt trauma or penetrating trauma).

In certain embodiments, the invention is drawn to a method of resuscitating a subject in need thereof. In specific embodiments, the invention is drawn administering a resuscitation fluid comprising a molecule that decreases or inhibits a biological activity of a bufadienolide. A "resuscitation fluid" refers to a liquid with the proper viscosity to be administered physiologically and is used to restore normal body parameters and functions, including, for example, blood pressure and/or blood volume. In particular embodiments, the resuscitation fluid of the invention affects Na/K ATPase activity in a cell following the onset of shock. Such activity may result in affecting homeostatic activities and function of a cell including, for example, an increase or maintenance of cell membrane potential, a decrease or maintenance in cell volume, and/or a decrease or maintenance in intracellular ions (including, for example, calcium ions).

In specific embodiments, the invention is drawn to administering a composition comprising a therapeutically effect amount of a molecule that decreases or inhibits a biological activity of a bufadienolide. A molecule of the invention possesses Na/K ATPase regulatory activity (including, for example, inhibits inhibitors of activity, inhibits activity, induces activity, maintains activity, inhibits inducers of activity, stimulates inhibitors of activity, or stimulates inducers of activity). In certain embodiments, a molecule of the invention inhibits inhibitors of Na/K ATPase activity thereby maintaining or restoring Na/K ATPase activity. A molecule of the invention includes any molecular entity including, for example, a small molecule, nucleic acid (such as, siRNA, shRNA expression cassette, antisense DNA, antisense RNA), protein, peptide, antibody, antisense drug, or other any biomolecule that is naturally made, synthetically made, or semi-synthetically made. In certain embodiments, a molecule of the invention includes an antibody. In specific embodiments, the antibody is a monoclonal antibody. In other specific embodiments, the antibody is a polyclonal antibody. A molecule of the invention can be used alone or in combination with another molecule or treatment that can alleviate, reduce, ameliorate, prevent, or maintain in a state of remission physiological effects or diagnostic markers associated with an alteration in Na/K ATPase activity. The invention also includes congers of bufalin that may antagonize the inhibatory effect that bufalin has on Na/K ATPase, including, for example, marinobufogenin, resibufogenin, or cinobufagin.

In specific embodiments, the invention is drawn to administering a composition comprising an antigenic agent that stimulates the host (human or animal) immune system thereby developing antibodies to prevent inhibition of Na/K ATPase.

In certain embodiments, the invention is drawn to inhibiting a biological activity of a bufadienolide. In specific embodiments, the biological activity of a bufadienolide includes, for example, decreasing or inhibiting Na/K ATPase activity.

In other specific embodiments, the bufadienolide is bufalin and/or bufalin sulfate. However, other bufadienolides of the invention include those that can inhibit the activity of Na/K ATPase, which include, for example, 19-norbufalin, 3,beta-OH-14,alpha-20:21-bufenolide, and proscillaridin-like inhibitor (see, for example, Eur. J. Biochem. (2002) 269: 2440-2448, which is incorporated by reference in its entirety herein). The methods and compositions of the invention also encompass inhibitors directed to other bufadienolides. The invention is drawn to any molecule that decreases or inhibits Na/K ATPase activity in response to any disease or other pathophysiological condition. For example, inhibitors of Na/K ATPase include, for example, cardiotonic steroid or steroid-like molecules including, for example, oubain, digoxin-like inhibitor, and PST 2238 (Id.).

B. Compositions of the Invention

Suitable pharmaceutical carriers, excipients and/or diluents are well known in the art and include phosphate buffered saline solutions, water, emulsions (including, for example, oil/water emulsions), various types of wetting agents, and sterile solutions. Compositions comprising pharmaceutical carriers, excipients and/or diluents can be formulated by well known conventional methods in the art. These compositions can be administered to the subject in need thereof at a suitable dose. Routes of administration of an active molecule and compositions of the invention include, for example, intraarterial administration, epicutaneous administration, eye drops, intranasal administration, intragastric administration (e.g., gastric tube), intracardiac administration, subcutaneous administration, intraosseous infusion, intrathecal administration, transmucosal administration, epidural administration, insufflation, oral administration (e.g., buccal or sublingual administration), oral ingestion, anal administration, inhalation administration (e.g., via aerosol), intraperitoneal administration, intravenous administration, transdermal administration, intradermal administration, subdermal administration, intramuscular administration, intrauterine administration, vaginal administration, administration into a body cavity, surgical administration (e.g., at the location of a tumor or internal injury), administration into the lumen or parenchyma of an organ, or other topical, enteral, mucosal, parenteral administration, or other method or any combination of the forgoing as would be known to one of ordinary skill in the art.

Regardless of the mode of administration, suitable compositions in accordance with the invention will generally include an amount of an active molecule admixed with an acceptable pharmaceutical carrier or diluent, such as a sterile aqueous salt solution, to give a range of final concentrations, depending on the intended use. It should be appreciated that endotoxin contamination should be kept minimally at a safe level (for example, less than 0.5 ng/mg protein). Moreover, for human administration, preparations should meet sterility, pyrogenicity, and general safety and purity standards as required by FDA Office of Biological Standards.

The dosage regimen will be determined by the attending physician in light of relevant clinical factors. As is well known in the medical arts, dosages for any one patient depends upon many factors, including patient size, body surface area, age, the particular molecule or composition to be administered, sex, time, route of administration, general health, and the presence of other molecules or compositions being administered concurrently. The compositions of the invention may be administered locally or systemically. The compositions of the invention may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the compositions of the invention may comprise further agents depending on the intended use of the composition.

The compositions of the present invention may be manufactured in a manner that is known in the art (including, for example, by means of conventional mixing, dissolving, granulating, dragee-making, levigating, emulsifying, encapsulating, entrapping, or lyophilizing processes). The compositions may be provided as a salt and can be formed with an acid (including, for example, hydrochloric acids sulfuric acid, acetic acid, lactic acid, tartaric acid, malic acid, and, succinic acid). Salts may tend to be more soluble in aqueous or other protonic solvents than are the corresponding free base forms. In other cases, the preferred preparation may be a lyophilized powder which may contain, for example, any or all of the following: 1-50 mM histidine, 0.1%-2% sucrose, and 2-7% mannitol, at a pH range of 4.5 to 5.5, that is combined with buffer prior to use. After compositions have been prepared, they can be placed in an appropriate container and labeled for treatment of an indicated condition. Compositions suitable for use in the invention include compositions wherein the active ingredients are contained in an effective amount to achieve the intended purpose. The determination of an effective dose is well within the capability of those skilled in the art. For any molecule, the therapeutically effective dose can be estimated initially either in cell culture assays (including, for example, cultured neuronal cells), cell lines, or in animal models (including, for example, animal models using a rodent rabbit, dog, sheep, monkey, or pig). The animal model may also be used to determine the appropriate concentration range and route of administration. Such information can then be used to determine useful doses and routes for administration in humans. Therapeutic efficacy and toxicity concentrations may be determined by standard pharmaceutical procedures in cell cultures or experimental animals (including, for example, ED50 [the dose therapeutically effective in 50% of the population] and LD50 [the dose lethal to 50% of the population]). The dose ratio between therapeutic and toxic effects is the therapeutic index, and it can be expressed as the ratio, LD50/ED50. Generally, compositions of the invention that exhibit large therapeutic indices are preferred. The data obtained from cell culture assays and animal studies is used in formulating a dose range for human use. The dosage contained in such compositions is preferably within a range of circulating concentrations that include the ED50 with little or no toxicity. The dosage varies within this range depending upon the dosage form employed, patient idiosyncrasies, and the route of administration. The exact dosage will be determined by the practitioner, in light of factors related to the subject that requires treatment. Dosage and administration are adjusted to provide sufficient levels of the active molecule or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy (see, for example, Remington's Pharmaceutical Sciences (Maack Publishing Co., Easton, Pa.), which is incorporated herein in its entirety, for pharmaceutically acceptable carriers, formulations, dosing, and the like).

B. Dosage

The compositions of the may be subdivided into unit doses containing appropriate quantities of the active component. The unit dosage form can be a packaged preparation, such as plastic containers or in vials or ampules. Also, the unit dosage can be a liquid based preparation or formulated to be incorporated into a diluent that, upon addition of the liquid based preparation, dilutes the active compound to therapeutically effective amount and/or dosage.

The therapeutically effective amounts or doses are readily determinable using an animal model, as shown in the studies detailed herein. For example, experimental animals induced into hemorrhagic shock may be used to optimize appropriate therapeutic doses prior to translating to a clinical environment by adjusting the doses, volume, and vehicles. Such animal models are known to be very reliable in predicting effective therapeutic strategies. Further, in determining therapeutically effective amounts of a molecule of the invention, Na/K ATPase activity can be quantified. It is known in the art that Na/K ATPase activity can be determined by using methods well known in the art such as, for example, a rubidium (Rb) assay. Specifically in the Rb assay, Na/K ATPase moves radioactive Rb into the cell (instead of potassium) and the amount of radiation in the cell is measured over time to determine Na/K ATPase activity. Another assay for the measurement of Na/K ATPase is one using paranitrophenyl phosphate (pNPP) as a substrate for soluble Dog kidney Na/K ATPase. The rate of conversion from pNPP to pNP+phosphate can be monitored by spectroscopy at wavelength 400 nm to determine Na/K ATPase activity.

The dosage administered to a patient (e.g., animal or human) will be dependent upon the response desired and may be dependent upon for example, the age, health, or weight of the subject. Further considerations may include, for example, frequency of treatment, therapeutic ratio, concurrent treatment, and like considerations. Dosage levels of an administered molecule of the invention can be, for example, 0.1-10 mg/kg in a resuscitation volume, which is the volume of blood estimated to have been lost during for example, hemorrhage or physical trauma. However, the skilled artisan is aware that the molecules of the invention will be administered in a manner compatible with the dosage formulation and in such amount as is therapeutically effective. In certain embodiments, the therapeutically effective amount is in the range where the concentration of antibody prevents 75% (IC75) or more of bufalin and/or bufalin sulfate inhibition of Na/K ATPase.

C. Methods of Use

I. General

Certain adverse clinical conditions and physiological effects result from an inhibition or a decrease in Na/K ATPase activity. These clinical conditions include, for example, shock (including hemorrhagic shock, septic shock, cardiogenic shock, and/or shock caused by the patient sustaining a physical trauma such as a blunt trauma or a penetrating trauma), and cardiac depression. A non-limiting example of a blunt trauma includes any sudden force applied to a body, which may cause bruising or bone breakage. Non-limiting examples of a penetrating trauma includes a gunshot wound, combat wound, or a knife wound.

Shock and cardiac depression may involve an abnormally low or depressed Na/K ATPase activity that is lower than under non-shock or cardiac depression conditions. Because the function of Na/K ATPase involves maintaining a chemical gradient of higher Na/lower K outside of the cell and lower Na/higher K inside of the cell inhibition of the Na/K ATPase enzyme leads to movement of Na and water into the cell. Consequently, the extracellular space and plasma space becomes depleted of water leading to a decrease in effective blood volume. In a state of decreased effective blood volume, the increased sequestration of Na and water augments the volume deficiency and leads to, for example, the clinical condition of shock. Monoclonal and polyclonal antibodies to bufalin or other molecules that inhibit bufalin activity can alleviate these adverse physiological effects by attenuating or preventing bufalin inhibition of Na/K ATPase activity (1-13).

In the presence of normovolemia, hypertension may result from inhibition of Na/K ATPase. Furthermore, inhibition of Na/K ATPase activity leads to a fall in membrane potential, which may cause or contribute to the causes of bipolar disorder (64,65), depression, schizophrenia (12,64), and diabetes (14,19). Because bufalin inhibits Na/K ATPase and has been found to be in mammals (37,42-46,48,51,52), bufalin polyclonal and monoclonal antibodies or other molecules that inhibit bufalin may alleviate these clinical disease conditions.

Jones et al., (21) demonstrated that a plasma fraction containing an inhibitor to Na/K ATPase depresses myocardial function and has negative inotropic and chronotropic effects on the heart. Because the invention is directed at maintaining or increasing Na/K ATPase activity in a cell, it is contemplated that the methods and compositions disclosed herein can be used to reverse or attenuate myocardial depression that occurs during sepsis or prolonged cardiac bypass.

II. Treatment of Shock

Certain embodiments of the invention teach a method for treating a mammal in shock comprising administering a therapeutically effective amount of a molecule of the invention. In particular embodiments, the form of shock is hemorrhagic shock, which can be presented clinically by a number of means. In an exemplary embodiment, an individual sustains a sudden violent wound, such as during combat, thereby losing a sufficient amount of blood to induce hemorrhagic shock as a result therefrom. The physiological adverse affects of shock include low or decreased blood volume and blood pressure, which is caused, at least in part, by a decrease in Na/K ATPase activity. Administering to this individual a molecule that increases Na/K ATPase activity or blocks a decrease or inhibition of Na/K ATPase activity reverses these adverse physiological effects and ultimately prevents death, which occurs in shock patients if left untreated.

In particular embodiments of the invention, the individual is a human, however, use in animals, including veterinary uses are contemplated and within the scope of the invention.

III. Treatment of Bipolar Disorder, Mental Depression, Schizophrenia, and Diabetes Bipolar disorder, depression, schizophrenia, and diabetes are clinical conditions reported to be due, at least in part, to a decrease in cellular membrane potential and/or an inability to maintain cellular membrane potential. Inhibition of Na/K ATPase activity leads to a decrease in cellular membrane potential and/or an inability to maintain cellular membrane potential. Monoclonal or polyclonal antibodies to bufalin or other molecules that inhibit bufalin activity can be used to alleviate or otherwise treat these clinical conditions as they will prevent or attenuate inhibition of Na/K ATPase activity that is present in these conditions.

IV. Perfusion of Excised Organs or Limbs for Transplant

Organs or limbs removed for transplant purposes degrade rapidly over time and can benefit from infusion of a resuscitation fluid comprising monoclonal and polyclonal antibodies to bufalin or other molecules that inhibit bufalin activity. Monoclonal or polyclonal antibodies to bufalin or other molecules that inhibit bufalin activity will prevent or attenuate inhibition of Na/K ATPase activity, thereby allowing the organ to survive longer during transport and transplantation surgery. The resuscitation fluid of the invention is also contemplated as useful in methods directed to preserving organs during harvesting, such as for an organ intended for a transplant, and before and during transplant.

In a non-limiting example, kidneys removed for transplant purposes are currently placed on ice and transported (sometimes thousands of miles over many hours) to a hospital and transplanted into a recipient. Viability of the organ is time dependent and organs "out of the body" for extended periods of time fail to function after transplant. Viability time is increased by continuous perfusion of the excised organ with a resuscitation fluid comprising a bufalin antibody or other molecule that inhibits bufalin activity, which stimulates Na/K ATPase activity. For example, increased kidney viability prior to transplantation is accomplished by cannulating the renal artery and perfusing the kidney with a resuscitation fluid comprising a bufalin antibody. In another non-limiting example, a severed limb from an accident victim is perfused with a resuscitation fluid comprising monoclonal or polyclonal antibodies to bufalin to increase viability until the limb can be surgically reattached to the accident victim. In this example, the artery of the limb is cannulated and the limb is perfused with a resuscitation fluid comprising a bufalin antibody using a pump.

While the invention has been described with reference to certain embodiments herein, those skilled in the art will appreciate that various modifications may be made without departing from the spirit and scope of the invention. The scope of the appended claims is not to be limited to the embodiments described herein.

EXAMPLES

As demonstrated herein, it was recently found that the bufadienolide, MBG, is elevated in the plasma in vivo during hemorrhagic shock (FIG. 1). Bufadienolides inhibits Na/K ATPase in a dose-dependant manner (FIG. 2). Bufalin or ouabain prevents restitution of blood volume after mild hemorrhage (FIG. 3). MBG did not have this effect. Furthermore, infusion of bufadienolide antibodies prolongs survival time in lethal hemorrhagic shock (FIG. 4). Furthermore, an affinity column made from the polyclonal antibodies (FIG. 4) captured 10× more bufalin than MBG. We have recently isolated bufalin sulfate in plasma of pig and rat by HPLC. Identification of Bufalin and bufalin sulfate from a single HPLC peaks was by Mass Spectroscopy. We also prepared a second affinity column with a monoclonal antibody directed against MBG, that bound MBG, resibufagenin and cinobufagenin, but not bufalin. This column did not retain any bufodienolide in the same samples. This suggests that an inhibitor of Na/K ATPase is secreted during lethal hemorrhage, and that the inhibitor is bufalin or bufalin sulfate. This is the first disclosure demonstrating that antibodies against bufalin prolong survival to hemorrhagic shock. In light of this, the use antibodies to bufalin as a resuscitation agent to prolong survival and/or alleviate detrimental symptoms in any disease state that is accompanied by inhibition of Na/K ATPase by bufalin or bufalin sulfate (including but not limited to, septic shock, cardiogenic shock, diabetes, mental depression, bipolar disorder and schizophrenia) is within the scope of the present invention.

Example 1

Rat Shock Model and Measurement of Bufadienolides

Sixteen male Sprague-Dawley Rats (300-380 g) were anesthetized with pentobarbital sodium (50 gm/kg) and cannulaes were placed in the femoral artery (PE-50) and vein (PE-90) for measurement of arterial blood pressure and blood withdrawal, respectively. After 15 min of stabilization, blood was drawn from the femoral vein until Mean Arterial Blood Pressure (MABP) reached 35 mmHg and was continually withdrawn to maintain the MABP at 35 mmHg. During this period, each rat defended pressure and blood was removed to maintain MABP at 35 mmHg. Blood samples were taken from the venous cannula at various times for determination of the plasma bufadienolide, MBG (currently, there is no assay for any of the other bufadienolides) and ouabain (FIG. 1). These data demonstrate that plasma bufadienolides levels increase upon conditions of profuse bleeding and hemorrhagic shock.

Example 2

Na/K ATPase Activity by pNPP

Na/K ATPase activity was determined by the conversion of pNPP (para nitrophenylphosphate to para nitrophenyl+phosphate using soluble dog Na/K ATPase (FIG. 2). 100 ul of Na/K buffer (395 nM NaCl, 75 mM KCl, 15 mM $MgSO_4$, 800 mM HEPES) was added to a 96 well microplate. Various concentrations of bufalin, marinobufogenin, resibufogenin, cinobufagin or Ouabain were added with 10 ul of 0.25 units/ml dog Na/K ATPase (SigmaAldrich). 20 ul of 0.1 mM ATP/70 mM $MgCl_2$ was added. 20 ul of pNPP (para nitrophenylphosphate, SigmaAldrich) was added. The 96 well plate was placed in a Spectrophotometer measuring wavelength 400 nm every 30 sec to obtain a rate of conversion of pNPP to pNP+phosphate by ATPase over 30 min. The rate of conversion is compared between different doses of bufalin, marinobufogenin, resibufogenin, cinobufagin or Ouabain (FIG. 2). These data demonstrate that bufadienolides inhibits Na/K ATPase activity directly.

Example 3

Inhibition of Na/K ATPase by Bufalin or Ouabain Contributes to Lethal Hemorrhage These experiments were conducted using a modification of the chronically cannulated rat originally described by Fagin, Shinsako and Dallman, Am. J. Physiol. 245:E515,1983. Male Sprague-Dawley rats weighing 300-400 g are anesthetized with pentobarbital sodium (50 mg/kg ip). The femoral artery and vein is exposed and cannulas are inserted. The femoral artery (Dural Plastics) and femoral vein (PE-50) cannulas are for measurement of arterial blood pressure and heart rate and for injection. The cannulas are tunneled under the skin of the back to exit at the back of the neck using a 10 gauge trokar. A Dacron felt covered end of a stainless steel spring was connected, under the skin at the back of the neck. The skin is sutured around the spring using 4-0 braded silk. Both cannulas traverse the spring to the top of the cage and are plugged. The other end of the spring is connected to the top of the cage by paper clips so as to allow full rotation of the spring and cannulas. The spring allows the rat full access to the cage and does not restrict movement. The spring protects the cannulas from the rat. Cannulas are flushed with heparenized saline (50 u/ml) as needed.

On the following day, the rats are randomly divided into 3 groups of eight. One group received a 20 ml/kg hemorrhage, a second group received an infusion of ouabain at a concentration of 2 mg/ml at 5 ml/hr, while the third group received both hemorrhage and ouabain. MABP and heart rate are measured throughout. Blood volume is determined by Evans Blue dye (1 mg injected in saline, before hemorrhage to determine before hemorrhage plasma volume) by dye dilution. Hematocrit is taken continually and Blood volume is determined before and at various times after hemorrhage as we have previously described (1,68-70).

Bufalin or Ouabain infusion bad no effect on plasma volume. Hemorrhage alone led to a fall in blood volume followed by a full recovery of blood volume. The combination of hemorrhage and bufalin or hemorrhage and ouabain (Na/K ATPase inhibition) led to a failure in blood volume recovery and, eventually, death (FIG. 3).

Example 4

Bufadienolide Mono- and Polyclonal Antibodies Prolong Survival in Hemorrhagic Shock Sixteen male Sprague-Dawley Rats (300-380 g) were anesthetized with pentobarbital sodium (50 gm/kg) and cannulaes were placed in the femoral artery (PE-50) and vein (PE-90) for measurement of arterial blood pressure and blood withdrawal, respectively. After 15 min of stabilization, blood was drawn from the femoral vein until Mean Arterial Blood Pressure (MABP) reached 35 mmHg and was continually withdrawn to maintain the MABP at 35 mmHg. During this period, each rat defended pressure and blood was removed to maintain MABP at 35 mmHg. When each rat failed to defend MABP (i.e., blood is no longer needed to be withdrawn to maintain MABP at 35 mmHg), an infusion of a volume equal to the volume lost containing either bufadienolide antibodies in saline (150 mM Na/Cl) or normal rabbit serum in saline (control for polyclonal antibodies) or 10 mM Tris in saline (control for monoclonal antibodies) was infused over 6-9 min. MABP and heart rate were recorded throughout and survival times were recorded. Rats receiving mono- or polyclonal antibodies to bufadienolides survived significantly longer (FIG. 4) then control rats (n=8 for each group). These data demonstrate that a resuscitation fluid comprising antibodies to bufadienolides is able to prolong survival in subjects under conditions of profuse bleeding and hemorrhagic shock.

REFERENCES

All patents and publications mentioned or cited in this specification are indicative of the level of those skilled in the art to which the invention pertains. All patents and publications mentioned or cited herein are incorporated by reference to the same extent as if each individual publication was specifically and individually indicated to be incorporated by reference.

PUBLICATIONS

1. Darlington D N, Chew G, Ha T, Keil L C, Dallman M F 1990 Corticosterone, but not glucose, treatment enables fasted adrenalectomized rats to survive moderate hemorrhage. Endocrinology 127:766-72.
2. Campion D S, Lynch L J, Rector F C, Jr., Carter N. Shires G T 1969 Effect of hemorrhagic shock on transmembrane potential. Surgery 66:1051-9.
3. Cunningham J N, Jr., Wagner Y. Shires G T 1970 Changes in intracellular sodium content of red blood cells in hemorrhagic shock. Surg Forum 21:38-40.
4. Shires G T, Cunningham J N, Backer C R, et al. 1972 Alterations in cellular membrane function during hemorrhagic shock in primates. Ann Surg 176:288-95.
5. Illner H P, Shires G T 1981 Membrane defect and energy status of rabbit skeletal muscle cells in sepsis and septic shock. Arch Surg 116:1302-5.
6. Illner H, Shires G T 1982 Changes in sodium, potassium, and adenosine triphosphate contents of red blood cells in sepsis and septic shock. Circ Shock 9:259-67.
7. Gallagher J F, Shires G T 1977 Correlation of transmembrane potential difference with high-energy phosphate levels in hemorrhagic shock. Surg Forum 28:19-21.
8. Peitzman A B. Shires G T. 3rd, Illner H, Shires G T 1981 Effect of intravenous ATP-MgCl2 on cellular function in liver and muscular in hemorrhagic shock. Curr Surg 38:300-4.
9. Shires G T, 3rd, Peitzman A B, Illner H. Shires G T 1983 Changes in red blood cell transmembrane potential, electrolytes, and energy content in septic shock. J Trauma 23:769-74.
10. Boulanger B R, Evans J A, Lilly M P, Shurtleff D M. Williams J C, Gann D S 1993 A circulating protein that depolarizes cells increases after hemorrhage in dogs. J Trauma 34:591-8: discussion 599.
11. Borchelt B D, Wright P A, Evans J A, Gann D S 1995 Cell swelling and depolarization in hemorrhagic shock. J Trauma 39:187-92; discussion 192-4.
12. Eastridge B J, Darlington D N, Evans J A, Gann D S 1994 A circulating shock protein depolarizes cells in hemorrhage and sepsis. Ann Surg 219:298-305.
13. Evans J A, Darlington D N, Gann D S 1991 A circulating factor(s) mediates cell depolarization in hemorrhagic shock. Ann Surg 213:549-56: discussion 556-7.
14. Kowluru R, Bitensky M W, Kowluru A, Dembo M, Keaton P A, Buican T 1989 Reversible sodium pump defect and swelling in the diabetic rat erythrocyte: effects on filterability and implications for microangiopathy. Proc Natl Acad Sci USA 86:3327-31.
15. Darlington D N, Gann D S 2005 Adenosine stimulates NA/K ATPase and prolongs survival in hemorrhagic shock. J Trauma 58:1-6.
16. Abdel-Zaher A O, Abdel-Aal R A, Aly S A, Khalifa M M 1996 Adenosine for reversal of hemorrhagic shock in rabbits. Jpn J Pharmacol 72:247-54.
17. Griffith D A, Jarvis S M 1996 Nucleoside and nucleobase transport systems of mammalian cells. Biochim Biophys Acta 1286:153-81.
18. Baldwin S A, Beal P R, Yao S Y, King A E, Cass C E, Young J D 2004 The equilibrative nucleoside transporter family, SLC29. Pflugers Arch 447:735-43.
19. Koc B, Erten V, Yilmaz M I, Sonmez A, Kocar I H 2003 The relationship between red blood cell Na/K-ATPase activities and diabetic complications in patients with type 2 diabetes mellitus. Endocrine 21:273-8.
20. Trunkey D D, Illner H, Wagner I Y, Shires G T 1979 The effect of septic shock on skeletal muscle action potentials in the primate. Surgery 85:638-43.
20. Jones R O, Carlson D E, Gann D S 1994 A circulating shock protein that depolarizes cells in vitro depresses myocardial contractility and rate in isolated rat hearts. J Trauma 37:752-8.
22. Blake P, Hasegawa Y, Khosla M C, Fouad-Tarazi F, Sakura N. Paganini E P 1996 Isolation of "myocardial depressant factor(s)" from the ultrafiltrate of heart failure patients with acute renal failure. Asaio J 42:M911-5.
23. Shah K J, Chiu W C, Scalea T M, Carlson D E 2002 Detrimental effects of rapid fluid resuscitation on hepatocellular function and survival after hemorrhagic shock. Shock 18:242-7.
24. Carrico C J, Coin C D, Lightfoot S A, Allsman A, Shires G T 1963 Extracellular Fluid Volume Replacement in Hemorrhagic Shock. Surg Forum 14:10-2.
25. Trunkey D D, Illner H, Wagner I Y, Shires G T 1973 The effect of hemorrhagic shock on intracellular muscle action potentials in the primate. Surgery 74:241-50.
26. Gala G J, Lilly M P, Thomas S E, Gann D S 1991 Interaction of sodium and volume in fluid resuscitation after hemorrhage. J Trauma 31:545-55: discussion 555-6.
27. Blaustein M P 1977 Sodium ions, calcium ions, blood pressure regulation, and hypertension: a reassessment and a hypothesis. Am J Physiol 232:C165-73.
28. Hamlyn J M, Blaustein M P, Bova S, et al. 1991 Identification and characterization of a ouabain-like compound from human plasma. Proc Natl Acad Sci USA 88:6259-63.
29. Ferrandi M, Manunta P, Balzan S, Hamlyn J M, Bianchi G, Ferrari P 1997 Ouabain-like factor quantification in mammalian tissues and plasma: comparison of two independent assays. Hypertension 30:886-96.
30. Rybakowski J K, Lehmann W 1994 Decreased activity of erythrocyte membrane ATPases in depression and schizophrenia. Neuropsychobiology 30:11-4.
31. Matsukawa M, Mukai T, Akizawa T, Miyatake S, Yoshioka M, Morris J F, Butler V P Jr. Isolation and characterization of novel endogenous digitalis-like factors in the ovary of the giant toad, Bufo marinus. J Nat Prod. 1998 December; 61(12): 1476-81.
32. Butler V P Jr, Morris J F, Akizawa T, Matsukawa M, Keating P. Hardart A, Furman I. Heterogeneity and lability of endogenous digitalis-like substances in the plasma of the toad, Bufo marinus. Am J Physiol. 1996 August; 271(2 Pt 2):R325-32.
33. Akimova O A, Bagrov A Y, Lopina O D, Kamernitsky A V, Tremblay J, Hamet P, Orlov S N. Cardiotonic steroids differentially affect intracellular Na+ and [Na+]i/[K+]i-independent signaling in C7-MDCK cells. J Biol Chem. 2005; 280(1):832-9.
34. Bagrov A Y, Roukoyatkina N I, Fedorova O V, Pinaev A G, Ukhanova M V. Digitalis-like and vasoconstrictor effects of endogenous digoxin-like factor(s) from the venom of Bufo marinus toad. *Eur J Pharmacol.* 1993; 234, 165-72
35. Xu W, Luo H, Zhang Y, Shan L, Li H, Yang M, Liu R, Zhang W. Simultaneous determination of five main active bufadienolides of Chan Su in rat plasma by liquid chromatography tandem mass spectrometry. Journal of Chromatography B., 2007:859, 157-163
36. Cao Y, Zhao L, Liang Q, Bi K, Wang Y, Luo G. Study of the determination and pharmacokinetics of bufadienolides in dog's plasma after administration of Liu-Shen-Wan by high performance liquid chromatography time-of-flight mass spectrometry. Journal of Chromatography B. 2007: 853, 227-233.
37. Bagrov A Y, Fedorova O V. Effects of two putative endogenous digitalis-like factors, marinobufagenin and ouabain, on the Na+, K+-pump in human mesenteric arteries. J Hypertens. 1998 December; 16(12 Pt 2):1953-8.
38. Lopatin D A, Ailamazian E K, Dmitrieva R I, Shpen V M, Fedorova O V, Doris P A, Bagrov A Y. Circulating bufodienolide and cardenolide sodium pump inhibitors in preeclampsia. J Hypertens. 1999 August; 17(8):1179-87.
39. Vu H V, Ianosi-Irimie M R, Pridjian C A, Whitbred J M, Durst J M, Bagrov A Y, Fedorova O V, Pridjian G, Puschett J B. Involvement of marinobufagenin in a rat model of human preeclampsia. Am J Nephrol. 2005; 25(5):520-8.
40. Fedorova O V, Kolodkin N I, Agalakova N I, Namikas A R, Bzhelyansky A, St-Louis J, Lakatta E G, Bagrov A Y. Antibody to marinobufagenin lowers blood pressure in pregnant rats on a high NaCl intake: J Hypertens. 2005; 23(4):835-42.
41. Puschett J B. The role of excessive volume expansion in the pathogenesis of preeclampsia. Med Hypotheses. 2006; 67(5):1125-32.
42. Anderson D E, Dhokalia A, Parsons D, Bagrov A Y. Sodium sensitivity in young adults with high resting end-tidal CO2. J Hypertens. 1998; 16(7):1015-22.
43. Fedorova O V, Lakatta E G, Bagrov A Y. Endogenous Na, K pump ligands are differentially regulated during acute NaCl loading of Dahl rats. Circulation. 2000; 102(24): 3009-14.
44. Fedorova O V, Talan M I, Agalakova N I, Lakatta E G, Bagrov A Y. Coordinated shifts in Na/K-ATPase isoforms and their endogenous ligands during cardiac hypertrophy and failure in NaCl-sensitive hypertension. J Hypertens. 2004; 22(2):389-97.
45. Fedorova O V, Talan M I, Agalakova N I, Lakatta E G, Bagrov A Y. Endogenous ligand of alpha(1) sodium pump, marinobufagenin, is a novel mediator of sodium chloride—dependent hypertension. Circulation. 2002; 105(9): 1122-7.
46. Fedorova O V, Kolodkin N I, Agalakova N I, Lakatta E G, Bagrov A Y. Marinobufagenin, an endogenous alpha-1 sodium pump ligand, in hypertensive Dahl salt-sensitive rats. Hypertension. 2001 February; 37(2 Part 2):462-6.
47. Periyasamy S M, Liu J. Tanta F. Kabak B, Wakefield B. Malhotra D, Kennedy D J. Nadoor A, Fedorova O V, Gunning W, Xie Z, Bagrov A Y, Shapiro J I. Salt loading induces redistribution of the plasmalemmal Na/K-ATPase in proximal tubule cells. Kidney Int. 2005; 67(5):1868-77.
48. Komiyama Y. Dong X H, Nishimura N, Masaki H, Yoshika M, Masuda M, Takahashi H. A novel endogenous 48. digitalis, telocinobufagin, exhibits elevated plasma levels in patients with terminal renal failure. Clin Biochem. 2005 January; 38(1):36-45.
49. Elkareh J, Kennedy D J, Yashaswi B, Vetteth S, Shidyak A, Kim E G, Smaili S. Periyasamy S M, Hariri I M, Fedorova L, Liu J. Wu L, Kahaleh M B, Xie Z. Malhotra D, Fedorova O V, Kashkin V A, Bagrov A Y, Shapiro J I. Marinobufagenin stimulates fibroblast collagen production and causes fibrosis in experimental uremic cardiomyopathy. Hypertension. 2007; 49(1):215-24.
50. Kennedy D J, Vetteth S, Periyasamy S M, Kanj M, Fedorova L, Khouri S, Kahaleh M B, Xie Z, Malhotra D, Kolodkin N I, Lakatta E G, Fedorova O V. Bagrov A Y, Shapiro J I. Central role for the cardiotonic steroid marinobufagenin in the pathogenesis of experimental uremic cardiomyopathy. Hypertension. 2006; 47(3):488-95.
51. Fridman A I, Matveev S A, Agalakova N I, Fedarova O V, Lakatta E G, Bagrov A Y. Marinobufagenin, an endogenous ligand of alpha-1 sodium pump, is a marker of congestive heart failure severity. J Hypertens. 2002; 20(6): 1189-94.
52. Gonick H C, Ding Y, Vaziri N D, Bagrov A Y, Fedorova O V. Simultaneous measurement of marinobufagenin, ouabain, and hypertension-associated protein in various disease states. Clin Exp Hypertens. 1998; 20(5-6):617-27.
53. Fedorova O V, Doris P A, Bagrov A Y. Endogenous marinobufagenin-like factor in acute plasma volume expansion. Clin Exp Hypertens. 1998 July-August; 20(5-6):581-91.
54. Bagrov A Y, Fedorova O V, Dmitrieva R I, French A W, Anderson D E. Plasma marinobufagenin-like and ouabain-like immunoreactivity during saline volume expansion in anesthetized dogs. Cardiovasc Res. 1996; 31(2):296-305.
55. Bagrov A Y, Fedorova O V, Dmitrieva R I, Howald W N, Hunter A P, Kuznetsova E A, Shpen V M. Characterization of a urinary bufodienolide Na+, K+-ATPase inhibitor in patients after acute myocardial infarction. Hypertension. 1998 May; 31(5): 1097-103.
56. Bagrov A Y, Kuznetsova E A, Fedorova O V. Endogenous digoxin-like factor in acute myocardial infarction. J Intern Med. 1994; 235(1):63-7.
57. Bagrov Y Y, Manusova N B, Egorova I A, Fedorova O V, Bagrov A Y. Endogenous digitalis-like ligands and Na/K-ATPase inhibition in experimental diabetes mellitus. Front Biosci. 2005; 10:2257-62.
58. Bagrov Y Y, Dmitrieva N I, Manusova N B, Zvartau E E, Patkina N A, Bagrov A Y. Involvement of endogenous digitalis-like factors in voluntary selection of alcohol by rats. Life Sci. 1999; 64(20):PL219-25.
59. Fedorova O V, Anderson D E, Bagrov A Y. Plasma marinobufagenin-like and ouabain-like immunoreactivity in adrenocorticotropin-treated rats. Am J Hypertens. 1998; 11(7):796-802.
60. Fedorova O V, Agalakova N I, Talan M I, Lakatta E G, Bagrov A Y. Brain ouabain stimulates peripheral marinobufagenin via angiotensin II signalling in NaCl-loaded Dahl-S rats. J Hypertens. 2005; 23(8):1515-23.
61. Fedorova O V, Lakatta E G, Bagrov A Y. Endogenous Na, K pump ligands are differentially regulated during acute NaCl loading of Dahl rats. Circulation. 2000; 102(24): 3009-14.
62. Fedorova O V, Talan M I, Agalakova N I, Droy-Lefaix M T, Lakatta E G, Bagrov A Y. Myocardial PKC beta2 and the sensitivity of Na/K-ATPase to marinobufagenin are reduced by cicletanine in Dahl hypertension. Hypertension. 2003; 41(3):505-11.
63. Bagrov A Y, Dinitrieva R I, Dorofeeva N A, Fedorova O V, Lopatin D A, Lakatta E G, Droy-Lefaix M T. Cicletanine reverses vasoconstriction induced by the endogenous sodium pump ligand, marinobufagenin, via a protein kinase C dependent mechanism. J Hypertens. 2000; 18(2): 209-15.
64. Christo P J, el-Mallakh R S 1993 Possible role of endogenous ouabain-like compounds in the pathophysiology of bipolar illness. Med Hypotheses 41:378-83.
65. El-Mallakh R S, Li R, Worth C A, Peiper S C 1996 Leukocyte transmembrane potential in bipolar illness. J Affect Disord 41:33-7.
66. Searle B M, Higashino H, Khalil F, et al. 1983 Vanadate effect on the Na, K-ATPase and the Na—K pump in in vitro-grown rat vascular smooth muscle cells. Circ Res 53:186-91.
67. Bukoski R D, Seidel C L, Allen J C 1983 Ouabain binding, Na+-K+-ATPase activity, and 86Rb uptake of canine arteries. Am J Physiol 245:H604-9.
68. Darlington D N, Jones R O, Magnuson T A, Gann D S 1995 Role of intestinal fluid in restitution of blood volume and plasma protein after hemorrhage in awake rats. Am J Physiol 268:R715-22.
69. Darlington D N, Jones R O, Marzella L, Gann D S 1995 Changes in regional vascular resistance and blood volume after hemorrhage in fed and fasted awake rats. J Appl Physiol 78:2025-32.
70. Darlington D N, Tehrani M J 1997 Blood flow, vascular resistance, and blood volume after hemorrhage in conscious adrenalectomized rat. J Appl Physiol 83:1648-53.

PATENTS

WO/2007/002638
U.S. Pat. No. 5,770,376
U.S. Pat. No. 5,756,353
U.S. Pat. No. 5,804,212
U.S. Pat. No. 5,725,871
U.S. Pat. No. 5,780,045

What is claimed:

1. A method of treating a pathological condition or disease caused by an alteration in Na/K ATPase activity in a subject in need thereof comprising administering a composition comprising a therapeutically effect amount of an antibody directed to bufalin and/or bufalin sulfate that inhibits a biological activity of bufalin and/or bufalin sulfate, wherein said pathological condition or disease caused by an alteration in Na/k ATPase activity is shock.

2. The method according to claim 1, wherein said alteration in Na/K ATPase activity is a decrease or inhibition in said activity.

3. The method according to claim 1, wherein said antibody directed to bufalin and/or bufalin sulfate and is selected from the group consisting of a polyclonal antibody, a monoclonal antibody, and an antigen binding fragment thereof.

4. The method according to claim 3, wherein said antibody directed to bufalin and/or bufalin sulfate is a polyclonal antibody.

5. The method according to claim 3, wherein said antibody directed to bufalin and/or bufalin sulfate is a monoclonal antibody.

6. The method according to claim 1, wherein said biological activity of bufalin and/or bufalin sulfate is an inhibition or decrease in Na/K ATPase, or is inhibited by vaccination or prior administration of antigen that evokes a host immune response.

7. A method of treating a physiological effect caused by an alteration in Na/K ATPase activity in a subject in need thereof comprising administering a composition comprising a therapeutically effect amount of an antibody directed to bufalin and/or bufalin sulfate that inhibits a biological activity of bufalin and/or bufalin sulfate, wherein said physiological effect caused by an alteration in Na/k ATPase activity is shock.

8. The method according to claim 7, wherein said alteration in Na/K ATPase activity is a decrease or inhibition in said activity.

9. The method according to claim 7, wherein said antibody directed to bufalin and/or bufalin sulfate and is selected from the group consisting of a polyclonal antibody, a monoclonal antibody, and an antigen binding fragment thereof.

10. The method according to claim 9, wherein said antibody directed to bufalin and/or bufalin sulfate is a polyclonal antibody.

11. The method according to claim 9, wherein said antibody directed to bufalin and/or bufalin sulfate is a monoclonal antibody.

12. The method according to claim 7, wherein said biological activity of bufalin and/or bufalin sulfate is an inhibition or decrease in Na/K ATPase, or is inhibited by vaccination or prior administration of antigen that evokes a host immune response.

13. A method of treating shock caused by an alteration in Na/K ATPase activity in a subject in need thereof comprising administering a therapeutically effect amount of an antibody directed to bufalin and/or bufalin sulfate that inhibits a biological activity of bufalin and/or bufalin sulfate.

14. The method according to claim 13, wherein said alteration in Na/K ATPase activity is an inhibition or decrease in said activity.

15. The method according to claim 13, wherein said antibody directed to bufalin and/or bufalin sulfate and is selected from the group consisting of a polyclonal antibody, a monoclonal antibody, and an antigen binding fragment thereof.

16. The method according to claim 15, wherein said antibody directed to bufalin and/or bufalin sulfate is a polyclonal antibody.

17. The method according to claim 15, wherein said antibody directed to bufalin and/or bufalin sulfate is a monoclonal antibody.

18. The method according to claim 13, wherein shock is selected from the group consisting of hemorrhagic shock, septic shock, cardiogenic shock, and shock resulting from physical trauma.

19. The method according to claim 13, wherein shock is hemorrhagic shock.

20. The method according to claim 13, wherein said biological activity of bufalin and/or bufalin sulfate is an inhibition or decrease in Na/K ATPase, or is inhibited by vaccination or prior administration of antigen that evokes a host immune response.

21. A method of resuscitating a subject in need thereof comprising administering a resuscitation fluid comprising a therapeutically effective amount of an antibody directed to bufalin and/or bufalin sulfate that inhibits a biological activity of bufalin and/or bufalin sulfate, wherein said subject is undergoing shock caused by an alteration in Na/k ATPase activity.

22. The method according to claim 21, wherein said antibody directed to bufalin and/or bufalin sulfate and is selected from the group consisting of a polyclonal antibody, a monoclonal antibody, and an antigen binding fragment thereof.

23. The method according to claim 22, wherein said antibody directed to bufalin and/or bufalin sulfate is a polyclonal antibody.

24. The method according to claim 22, wherein said antibody directed to bufalin and/or bufalin sulfate is a monoclonal antibody.

25. The method according to claim 21, wherein said biological activity of bufalin and/or bufalin sulfate is an inhibition or decrease in Na/K ATPase, or is inhibited by vaccination or prior administration of antigen that evokes a host immune response.

* * * * *